US009486561B2

(12) United States Patent
Walti et al.

(10) Patent No.: US 9,486,561 B2
(45) Date of Patent: Nov. 8, 2016

(54) SUCTION APPARATUS WITH A FLUSHABLE DRAINAGE LINE

(71) Applicant: Medela Holding AG, Baar (CH)

(72) Inventors: Martin Walti, Zurich (CH); Hilmar Ehlert, Hergiswil (CH)

(73) Assignee: Medela Holding AG, Baar (CH)

( * ) Notice: Subject to any disclaimer, the term of this patent is extended or adjusted under 35 U.S.C. 154(b) by 506 days.

(21) Appl. No.: 13/939,369

(22) Filed: Jul. 11, 2013

(65) Prior Publication Data
US 2014/0163489 A1 Jun. 12, 2014

(30) Foreign Application Priority Data
Dec. 7, 2012 (CH) ...................... 2732/12

(51) Int. Cl.
*A61M 1/00* (2006.01)
*A61L 9/015* (2006.01)
*A61L 9/16* (2006.01)
*A61L 9/20* (2006.01)

(52) U.S. Cl.
CPC ............. *A61M 1/0023* (2013.01); *A61L 9/015* (2013.01); *A61L 9/16* (2013.01); *A61L 9/20* (2013.01); *A61M 1/0052* (2014.02); *A61M 1/0054* (2014.02); *A61M 1/0058* (2013.01); *A61M 1/0088* (2013.01); *A61L 2209/11* (2013.01); *A61L 2209/212* (2013.01); *A61M 1/0084* (2013.01)

(58) Field of Classification Search
CPC . A61L 9/20; A61L 2209/212; A61M 1/0052
See application file for complete search history.

(56) References Cited

U.S. PATENT DOCUMENTS

| 5,738,656 | A | 4/1998 | Wagner |
| 2004/0193218 | A1 | 9/2004 | Butler |
| 2006/0155260 | A1 | 7/2006 | Blott |
| 2010/0078574 | A1 | 4/2010 | Cooper |
| 2012/0275954 | A1* | 11/2012 | Olson ............... A61L 2/208 422/33 |

FOREIGN PATENT DOCUMENTS

| EP | 2170022 | 3/2010 |
| WO | 98/10774 | 3/1998 |
| WO | 2005/061025 | 7/2005 |
| WO | 2007/087810 | 8/2007 |
| WO | 2012/067918 | 5/2012 |

OTHER PUBLICATIONS

International Search Report CH 27322012.

* cited by examiner

*Primary Examiner* — Leslie Deak
*Assistant Examiner* — Kai Weng
(74) *Attorney, Agent, or Firm* — McDonnell Boehnen Hulbert & Berghoff LLP

(57) ABSTRACT

A suction apparatus for aspirating a fluid from a human or animal body by negative pressure comprises a drainage connection for a drainage line in order to remove the fluid from the body. A vacuum source generates a negative pressure at the drainage connection. A fluid connection container collects the sucked-up fluid. The drainage line can be flushed with air by an auxiliary connection and an auxiliary line connected to the latter. In order to reduce the entraining of pathogens, a sterilizing cell is provided. The supplied air is treated in the latter in such a manner that pathogens contained in the air are modified and thereby rendered harmless.

26 Claims, 4 Drawing Sheets

SUCTION APPARATUS WITH A FLUSHABLE DRAINAGE LINE

CROSS-REFERENCE TO RELATED APPLICATIONS

This application claims the benefit of Swiss Patent Application Serial No. 2732/12 filed Dec. 7, 2012, the contents of which are fully incorporated herein by reference.

TECHNICAL FIELD

The present invention relates to a suction apparatus for aspirating a fluid from a human or animal body by means of negative pressure. Suction apparatuses of this type are used, for example, for pleura drainage, for drainage of the mediastinum, for drainage of wounds after injuries or operations, or for liposuction. The present invention also relates to a sterilizing device for use with a suction apparatus of this type and to a method for supplying sterilized air to such a suction apparatus.

BACKGROUND

Drainage pump systems are frequently used in the medical sector in order to aspirate body fluids and other fluids. Said systems customarily have a suction pump, one or more fluid collection containers and a drainage tube between the patient and the fluid collection container. By generation of a negative pressure in the fluid collection container, fluid is sucked from the patient via the drainage tube into the fluid collection container where it is collected.

It is known in addition to the drainage tube to carry an auxiliary tube to the patient. This enables air to be supplied to the patient's cavity which is to be drained, and the drainage line can be flushed. A drainage pump system with an auxiliary line is known, for example, from WO 2005/061025. U.S. Pat. No. 5,738,656 also discloses a drainage pump system with an auxiliary line. A bacteria filter is provided in the auxiliary line in said document.

US 2006/0155260 discloses a wound drainage system in which the wound is flushed with a flushing liquid, the flushing liquid is sucked off together with the wound exudate and is cleaned, and the cleaned flushing liquid is supplied again to the wound, in a closed circuit. The flushing liquid can be sterilized by the action of ultraviolet, gamma or electron radiation. WO 2012/067918 proposes sterilizing the sucked-off liquid in a drainage pump system by the action of ultraviolet radiation before or after said liquid enters the fluid collection container. The liquid treated in such a manner is subsequently disposed of.

SUMMARY OF THE INVENTION

It is an object of the present invention to provide a suction apparatus for body fluids, wherein air can be guided through an auxiliary line to the drainage line, and wherein the risk of the patient suffering infections because of this air is reduced.

A suction apparatus for aspirating a fluid from a human or animal body by means of negative pressure is proposed. The suction apparatus comprises:
  a drainage connection for a drainage line for removing the fluid from the body;
  a vacuum source for generating a negative pressure in order to suck off the fluid through the drainage line;
  a fluid collection container for collecting the fluid sucked up by the drainage line; and
  an auxiliary connection for an auxiliary line.

The suction apparatus further comprises a sterilizing device with a sterilizing cell. The sterilizing cell has an inlet in order to supply a gas which is still untreated, in particular air, to the sterilizing device. The sterilizing device is designed to treat the gas supplied to the sterilizing cell in such a manner that pathogens contained in said gas are modified and thereby rendered harmless, in particular in that germs contained in the gas are killed. The sterilizing cell further has an outlet in order to conduct the treated gas to the auxiliary connection. Outlet and inlet can be physically formed by the same opening in the sterilizing cell, but in one embodiment are formed by separate openings.

The sterilizing device accomplishes far more than a simple bacteria filter can accomplish: it does not simply filter out certain pathogens but rather modifies pathogens permanently in such a manner that they are rendered harmless, i.e. the pathogenecity thereof is reduced. In particular, the sterilizing device permanently kills germs (pathogens capable of replication) or prevents the replication capability thereof. As a result, the sterilizing device sustainably reduces contamination of the gas by pathogens and thus reduces the entraining of pathogens into the auxiliary line. In addition, pathogens which would penetrate through a bacteria filter can thereby also be removed. An entraining of pathogens into the subsequent lines is thus more effectively and more sustainably avoided than by means of a bacteria filter. This reduces the risk of the patient being infected by the supplied gas. The term "pathogens" is understood as including, in particular, bacteria, protozoa, viruses, prions and fungal spores.

The supplied gas is ambient air (fresh air) in one embodiment. For this purpose, in an example embodiment, the inlet is connected to the environment in order to supply the ambient air to the sterilizing cell. For this purpose, an air supply opening which leads to the environment and which is connected to the inlet of the sterilizing cell can be present on the housing of the suction apparatus or of the sterilizing device. In one embodiment, if the vacuum source is a pump, the sterilizing cell is therefore not supplied with the exhaust air, which is removed by the pump, from the fluid collection container, as would be the case in a closed circuit, but rather with fresh air, the contamination of which with pathogens is generally lower than the exhaust air from the fluid collection container. However, it is also conceivable to supply exhaust air to the sterilizing cell, wherein said exhaust air is subsequently supplied again to the body or output to the environment.

The gas supplied to the sterilizing cell is exposed to an external action of physical and/or chemical nature in order to kill the germs contained therein. In various example embodiments, the sterilizing device comprises a treatment device in order to treat the supplied gas by means of physical actions, such as by UV rays, gamma rays, electron rays (for example beta radiation), by increasing the temperature, and/or by the action of steam. For this purpose, the sterilizing device can comprise at least one UV light source, at least one heat source and/or at least one steam generator as a treatment device. However, alternatively or additionally, chemical actions, in particular ozonization, are also conceivable. For this purpose, the sterilizing device can comprise an ozone generator.

In an example refinement, the sterilizing device comprises at least one inlet valve at the inlet of the sterilizing cell, through which inlet valve the gas can be supplied to the sterilizing cell, and at least one outlet valve at the outlet of the sterilizing cell, through which outlet valve the treated gas can be conducted out of the sterilizing cell. The suction apparatus can also comprise a control device which is designed to carry out the following steps:
(a) closing the outlet valve;
(b) opening the inlet valve in order to supply the gas to the sterilizing cell;
(c) closing the inlet valve;
(d) treating the supplied gas in the sterilizing cell in such a manner that pathogens contained in said gas are modified and thereby rendered harmless; and
(e) opening the outlet valve in order to conduct the treated gas out of the sterilizing cell.

In this case, step (b) is carried out before, during or after step (a), i.e. the inlet valve can be opened while the outlet valve is still open; it can be opened at the same time as the closing of the outlet valve, or it can be opened only when the outlet valve is closed. The last variant is preferred, i.e. the valves preferably act as a lock for the entering gas. Step (c) is carried out after step (b), and step (d) (i.e. the treatment of the gas) is carried out at least in a part of the period of time between step (c) and step (e), but may also begin beforehand and/or end thereafter. Between step (c) and the end of step (d) there are typically a few seconds to some minutes, for example 1 second to 10 minutes. Under some circumstances, between the end of step (d) and step (e), there can be an extended period of time in which the treated gas remains in the sterilizing cell.

In order to improve the throughput of gas, the sterilizing cell can have a variable volume. This makes it possible to eject the treated gas as completely as possible from the sterilizing cell and to take up as large a quantity as possible of untreated gas again. In order to change the volume of the sterilizing cell, the sterilizing cell can have a cylindrical wall region and a plunger which is displaceable therein. It is also conceivable for the sterilizing cell to have an expansion-bellows-type wall region in order to change the volume of the sterilizing cell. However, the sterilizing cell can also have an elastic wall region and, in particular, can be designed in the manner of a balloon.

The volume of the sterilizing cell can be changeable passively by the volume changing depending on the gas pressure in the sterilizing cell. In order to assist the taking-up of the gas in the sterilizing cell, at least one spring element can be provided, which spring element is designed and arranged in such a manner that it tends to maximize the volume. As a result, the sterilizing cell can be operated in such a manner that, upon application of a sufficiently great negative pressure in relation to the ambient pressure below a certain pressure threshold, the volume is automatically reduced counter to the spring force because of the pressure differential in relation to the environment and is increased again on account of the spring force upon a rise in pressure.

However, the volume of the sterilizing cell can also be changeable actively. As a result, it is possible to take up untreated gas in a targeted manner irrespective of the remaining operating state of the suction apparatus, and/or to eject treated gas in a targeted manner and, for example, at a predeterminable pressure or a predeterminable rate. For this purpose, the sterilizing device can comprise a drive in order to actively change the volume of the sterilizing cell. This may be, for example, an electric motor drive or pneumatic drive.

However, in other embodiments, it is also possible for the sterilizing cell to have a constant volume.

The sterilizing cell can be designed and arranged in such a manner that a continuous, in particular substantially constant, volumetric flow can pass through said sterilizing cell, wherein the gas passing through the sterilizing cell is continuously treated. In this respect, the sterilizing cell can be designed as a continuous flow cell.

In one embodiment, an electrically operated pump (for example a diaphragm pump) serves as the vacuum source of the suction apparatus. Instead, however, it is possible, for example, for a vacuum regulator to be provided for connection to a hospital vacuum system (for example via a wall connection) or for a Venturi system to be provided, as is well known from the prior art, in order to generate the negative pressure.

The suction apparatus can be completed by a drainage line which is connected to the drainage connection, and by an auxiliary line which is connected to the auxiliary connection. In one example embodiment, an apparatus-remote end (i.e. close to the body during operation) of the auxiliary line is then in fluid-communicating connection with an apparatus-remote end of the drainage line. For this purpose, a direct connection can be provided between the apparatus-remote ends of the two lines, or the connection can be accomplished, for example, via a cavity of the patient by the two ends ending close to each other in the same cavity. The sterilized air from the sterilizing cell can then serve in particular to flush the auxiliary line and, as a result, also the drainage line and optionally to convey accumulations of solids, which could otherwise lead to clogging, in the direction of the fluid collection container.

The sterilizing cell or even the entire sterilizing device can be integrated into the pumping unit of the suction apparatus. For this purpose, the suction apparatus can have a pump assembly housing in which the pump is arranged, and the sterilizing cell or the entire sterilizing device is then likewise arranged in the pump assembly housing and can in particular be completely accommodated in the latter. However, the sterilizing cell or the entire sterilizing device may also be fastenable, for example, externally to the pump assembly housing. The sterilizing device can form an independent, self-contained unit. The sterilizing cell or the entire sterilizing device can be retrofittable and/or interchangeable.

The present invention also relates to a sterilizing device as such. A sterilizing device which is suitable for a suction apparatus for aspirating a fluid from a human or animal body by means of negative pressure is therefore provided. The sterilizing device comprises a sterilizing cell which is provided with an inlet in order to supply a gas which is still untreated to the sterilizing cell. The sterilizing device is designed to treat the supplied gas in such a manner that pathogens contained in said gas are modified and thereby rendered harmless. In addition, the sterilizing cell has an outlet in order to conduct the treated air out of the sterilizing cell.

The above considerations regarding the suction apparatus also apply analogously to the sterilizing device by itself. In particular, the supplied gas can be ambient air, and the inlet can accordingly be connected to the environment in order to supply ambient air to the sterilizing device. However, it is also conceivable to supply exhaust air from the suction apparatus to the sterilizing cell, wherein said exhaust air is subsequently supplied again to the body or is output to the external space. The sterilizing device can comprise a treatment device in order to treat the supplied gas in the above-mentioned manner, in particular by means of UV rays, by increasing the temperature and/or by the action of steam. It can comprise an inlet valve through which the gas can be supplied to the sterilizing cell, and an outlet valve through which the treated gas can be conducted out of the sterilizing cell. As described in more detail above, the sterilizing cell can have a variable volume. The volume can be changeable passively or actively in the manner described above.

In addition, the present invention relates to a method for supplying sterilized gas to an auxiliary line of a suction apparatus, wherein the suction apparatus has a drainage line in order to aspirate a fluid from a human or animal body by means of negative pressure, and wherein an apparatus-remote end of the auxiliary line is in fluid-communicating connection with an apparatus-remote end of the drainage line. The method comprises:
  supplying a gas to a sterilizing cell;
  treating the supplied gas in the sterilizing cell in such a manner that pathogens contained in said gas are changed and thereby rendered harmless; and
  conducting the treated gas out of the sterilizing cell to the auxiliary line.

In an example embodiment, the gas is ambient air, i.e. ambient air may be supplied from the environment to the sterilizing cell. However, it is also conceivable to supply exhaust air from the suction apparatus to the sterilizing cell, wherein said exhaust air is subsequently supplied again to the body or is output to the environment. As explained in more detail above, the supplied gas can be treated, for example, by means of UV rays, by increasing the temperature and/or by the action of steam.

If the gas is supplied to the sterilizing cell by an inlet valve, and if the treated gas is conducted out of the sterilizing cell by an outlet valve, the method can in particular comprise the following steps:
(a) closing the outlet valve;
(b) opening the inlet valve in order to supply the gas to the sterilizing cell;
(c) closing the inlet valve;
(d) treating the supplied gas in the sterilizing cell in such a manner that pathogens contained in said gas are changed and thereby rendered harmless; and
(e) opening the outlet valve in order to conduct the treated gas out of the sterilizing cell.

The same considerations which have been explained above in conjunction with the suction apparatus apply in respect of the sequence of said steps.

In the method, provision can be made for the volume of the sterilizing cell to be changeable while the gas is being supplied to the sterilizing cell and/or while the treated gas is being conducted out of the sterilizing cell. This can be accomplished passively by generation of corresponding pressure differentials or actively by means of a drive, as has been explained in more detail above.

BRIEF DESCRIPTION OF THE DRAWINGS

Example embodiments of the invention are described below with reference to the drawings which serve merely for explanation and should not be interpreted as being limiting. In the drawings.

DETAILED DESCRIPTION

Figure 1:
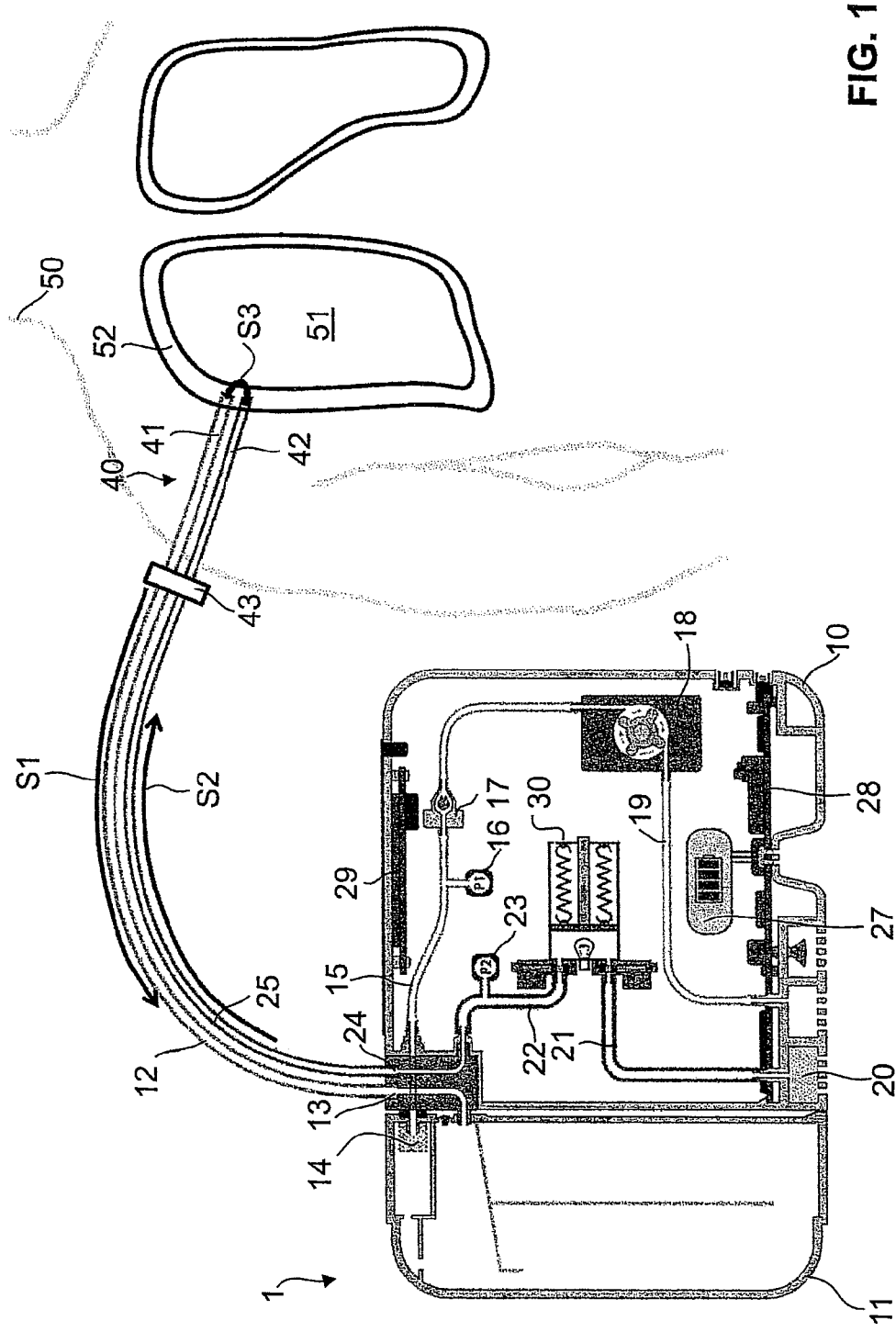
FIG. 1 shows a schematic illustration of a first exemplary embodiment of a suction apparatus with a sterilizing cell during the use for pleura drainage.

FIG. 1 illustrates a first embodiment of a suction apparatus according to the invention. The suction apparatus is designed as a compact, portable, battery-operated, digital thorax drainage apparatus. It comprises a pump assembly housing 10 to which a fluid collection container 11 is releasably connected. A drainage tube 12 opens via a connecting adapter into the fluid collection container 11, a drainage connection 13 for the drainage tube 12 being formed on the connecting adapter. A negative pressure is generated in the fluid collection container 11 by means of a suction pump 18 via a filter 14 and a vacuum line 15. A one-way valve 17 prevents air from passing back from the vacuum pump into the fluid collection container 11. The pressure P1 in the vacuum line 15 can be determined by means of a pressure transducer (manometer) 16. The air sucked up by the suction pump 18 is exhausted to the environment via an exhaust air line 19. In the present example, the suction pump 18 is a motor-operated, electric vacuum pump, in particular a diaphragm pump of a known type.

The pump assembly housing 10 accommodates a sterilizing cell 30, which is described in more detail below in conjunction with FIG. 2. Fresh air is supplied from the environment to the sterilizing cell 30 via an inlet filter 20, which is provided in an opening in the housing wall of the pump assembly housing 10, and an inlet line 21. The air treated in the sterilizing cell is conducted via an outlet line 22 to an auxiliary connection 24 for an auxiliary tube 25. The pressure P2 in the outlet line 22 can be determined by an optional pressure transducer 23.

In addition, further components which serve for the operation of the suction apparatus are arranged in the pump assembly housing 10. In particular, a rechargeable battery 27, a digital control device 28 and a display 29 are present. The control device 28 receives, inter alia, the measured values from the pressure transducers 16 and 23, controls the operation of the suction pump 18 and outputs information regarding the operating status to the display 29.

A double-lumen catheter 40 is connected to the apparatus-remote ends of the drainage tube 12 and of the auxiliary tube 25 via a coupling connector 43. The catheter 40 has a drainage lumen 41 which is connected to the drainage tube 12, and an auxiliary lumen 42 which is connected to the auxiliary tube 25. The drainage tube 12 and the drainage lumen 41 of the catheter 40 together form a drainage line, while the auxiliary tube 25 and the auxiliary lumen 42 together form an auxiliary line. The drainage line 12, 41 and the auxiliary line 25, 42 are in fluid-communicating connection at the apparatus-remote (body-near) end thereof, as indicated in FIG. 1 by the double arrow S3. While the connection in the present simplified example is accomplished outside the catheter 40, a direct connection between the two lumina 41, 42 can also be provided within the catheter 40.

In the present example, the suction apparatus serves for thorax drainage (pleura drainage). For this purpose, the catheter 40 opens into the pleural cavity 52, which surrounds a lung 51 of a patient 50. The suction apparatus serves to generate a negative pressure in the pleural cavity 52 in order to close the pleura gap and in order to aspirate wound secretions from the pleural cavity 52. For this purpose, during normal operation, the suction pump 18 is operated in such a manner that it generates a negative pressure in the fluid collection container 11. Air and wound secretions are thereby sucked off into the fluid collection container 11 via the drainage line 12, 41 (arrow S1). In the fluid collection container 11, liquid and solid constituents are separated from the sucked-up air, and only the sucked-up air passes via the filter 14 and the vacuum line 15 to the suction pump 18 and is conducted to the outside via the exhaust line 19.

In order to flush the drainage line 12, 41, sterilized air can be conducted via the auxiliary line 25, 42 from the sterilizing cell 30 to the apparatus-remote end of the drainage line 12, 41 (arrow S2). Said air enters the drainage line 12, 41, is sucked up by the suction pump 18 and thereby flushes the drainage line 12, 41. As a result, solid constituents in the drainage line 12, 41 are entrained and occlusions of the drainage line avoided. One possible sequence of such a flushing operation is explained in more detail below in conjunction with FIG. 4.

Figure 2:
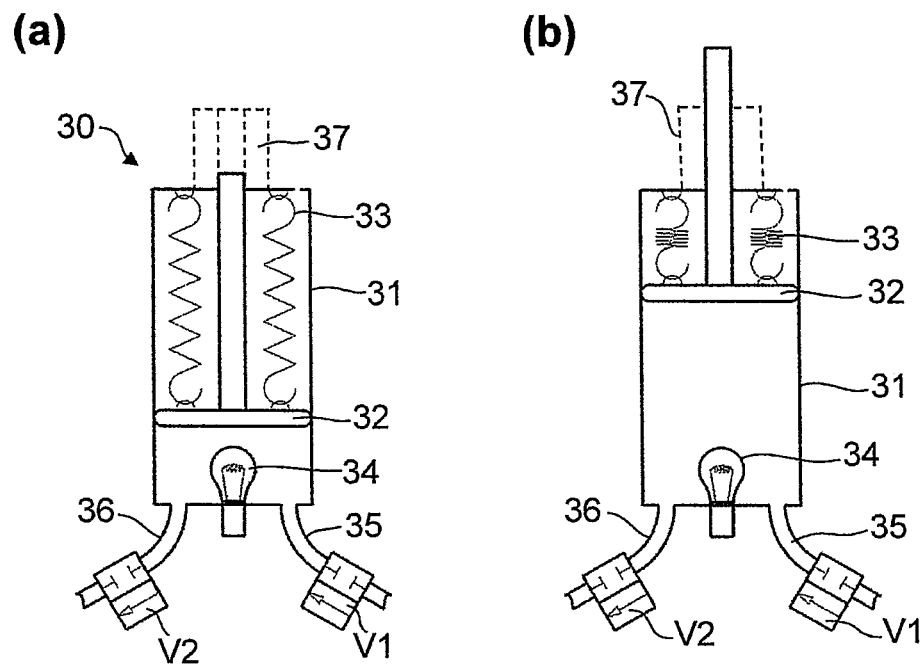
FIG. 2 shows a schematic illustration of the sterilizing cell of the suction apparatus of FIG. 1 (part (a): starting position; part (b): sterilizing position)

FIG. 2 illustrates the sterilizing cell 30 mentioned. The latter has a cylindrical side wall region 31 and a plunger 32 which is displaceable in a sealing manner therein. A changeable volume is thereby formed in the sterilizing cell. By means of a spring arrangement 33, the plunger 32 is preloaded in the direction of an increased volume. The spring arrangement acts here as a tension spring. However, it is also possible, for example, for a compression spring to be provided in the interior of the sterilizing cell. The sterilizing cell 30 has an inlet 35, at which an inlet valve V1 is arranged, and also an outlet 36, at which an outlet valve V2 is arranged. The sterilizing cell contains a heat source 34, which is indicated here symbolically by a bulb, as the treatment device. The heat source can be any type of heating element which is known per se, in particular a thick film heater, an infrared radiation source or any other means for heating the volume of air bounded by the side wall region 31 and plunger 32. The volume of air is preferably heated to a temperature of at least 70° C., preferably at least 100° C., in particular preferably at least 120° C. Germs in the volume of air are thereby killed. A temperature sensor can be provided in the sterilizing cell for monitoring purposes.

Figure 3:
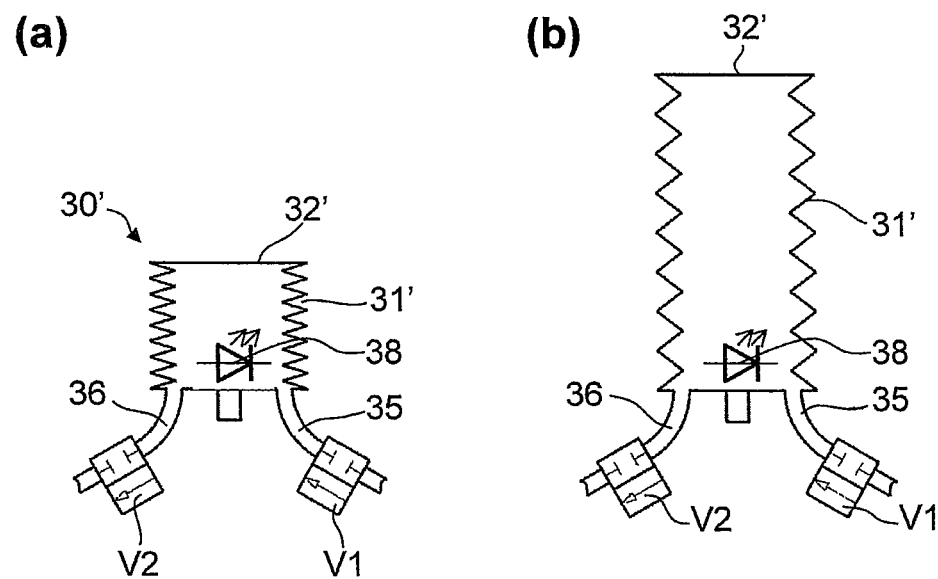
FIG. 3 shows a schematic illustration of a further embodiment of a sterilizing cell (part (a): starting position; part (b): sterilizing position)

A further variant of a sterilizing cell 30' is illustrated in FIG. 3. Said sterilizing cell 30' also has a changeable volume. For this purpose, the sterilizing cell 30' is provided with an expansion-bellows-type wall region 31'. As a result, the distance of a cover wall 32' of the sterilizing cell 30' from the inlet 35 and outlet 36 can be changed in order to change the volume of air accommodated in the sterilizing cell. Also in this variant, it is optionally possible to provide a spring arrangement which acts on the cover wall 32' and tends to maximize the volume of the sterilizing cell, or the expansion-bellows-type wall region 31' can be designed in such a manner that it generates a spring force of this type. Instead of a heat source 34, a UV source 38, which is merely indicated schematically as a UV light-emitting diode in FIG. 3, is arranged as the treatment device in the sterilizing cell 30'. Instead of a UV light-emitting diode, the UV source can also be a gas discharge lamp emitting UV radiation or any other source of UV light of sufficient intensity. The UV source can also be arranged outside the actual sterilizing cell if the sterilizing cell has a UV-permeable window. The UV light generated kills germs in the sterilizing cell.

Of course, a UV light source can also be used in a sterilizing cell with a moveable plunger, as in FIG. 2, and a heat source can also be used in a sterilizing cell with an expansion-bellows-type side wall region. Alternatively or in addition, it is also conceivable, for example, to provide a steam generator which pumps hot steam into the sterilizing cell, to provide an ozone generator which introduces ozone into the sterilizing cell, or to provide an electron source or a gamma radiation source.

Figure 4:
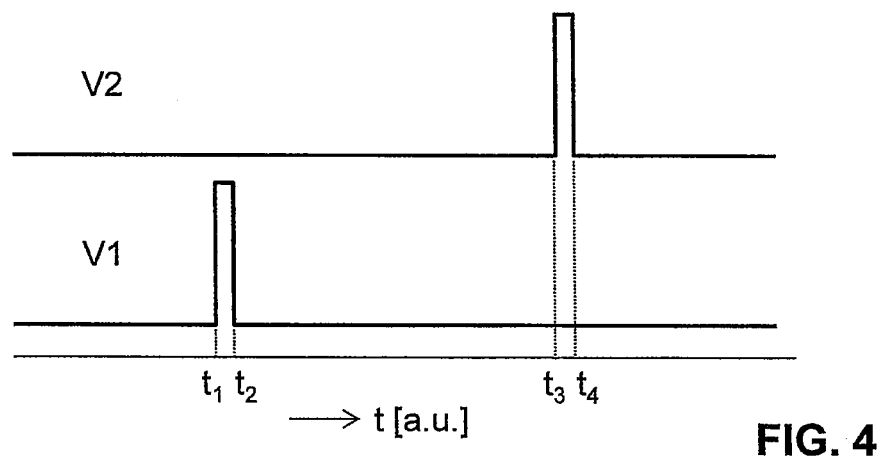
FIG. 4 shows a diagram for illustrating the sequence of states of the valves at the inlet and outlet of the sterilizing cell.

The manner in which the sterilizing cell of FIGS. 2 and 3 can be operated is illustrated in FIG. 4. At the beginning, a negative pressure prevails in the sterilizing cell. As a result, the sterilizing cell is in a state with a minimized volume (FIGS. 2(a) and 3(a)). The valve V1 is then opened at a time $t_1$. Air can thereby flow from the environment through the inlet 35 into the sterilizing cell 30. Owing to this equalization of the pressure, the sterilizing cell adopts a state in which the volume thereof is maximized (FIG. 2(b)) and FIG. 3(b)). In the process, the sterilizing cell is assisted by the spring arrangement. The valve V1 is then closed again at a time $t_2$. The treatment device in the form of the heat source 34 or the UV source 38 is then activated in order to kill pathogens which have possibly entered the sterilizing cell with the sucked-up air. After an action time of sufficient length, the treatment device is deactivated again, and it is optionally waited until the air in the sterilizing cell has cooled down again. At a time $t_3$, the outlet valve V2 is opened. The sterilizing cell is then in connection with the drainage line 12, 41 via the outlet line 22, the auxiliary connection 24 and the auxiliary line 25, 42. The drainage line 12, 41 is thereby flushed as described above. At the same time, a negative pressure arises in the sterilizing cell, leading to the sterilizing cell returning to the starting state thereof, with a minimized volume (FIG. 2(a) and FIG. 3(a)). The outlet valve V2 is closed again at a time $t_4$, and a new sterilizing cycle can begin.

The sterilizing cell can optionally be equipped with a drive 37, as illustrated by dashed lines in FIG. 2. The drive 37 makes it possible to actively change the volume of the sterilizing cell. For this purpose, for example, the displaceable plunger 32 can be provided with a plunger rod which is in the form of a rack, wherein a driving motor drives said rack in order to actively displace the plunger 32 in the side wall region 31. In the configuration in FIG. 3, a plunger rod can also act on the cover wall 32' instead of on the plunger 32. The drive 37 firstly serves to actively assist the sucking-in of air from the environment through the inlet line 21. Secondly, the drive can be used to actively eject the air, which is accommodated in the sterilizing cell, after the treatment. A positive pressure (for example a pressure pulse) can thereby be generated, for example transiently, in the auxiliary line 25, 42, the positive pressure leading to the pressure differential between the body-close end of the drainage line 12, 41 and the fluid collection container being increased transiently. This assists the transport of tissue clots or other material in the direction of the fluid collection container 11.

Figure 5:
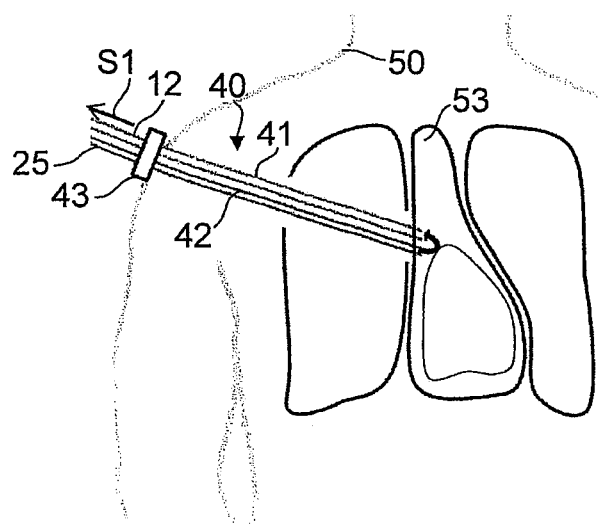
FIG. 5 shows a schematic illustration of drainage of the mediastinum.
Figure 6:
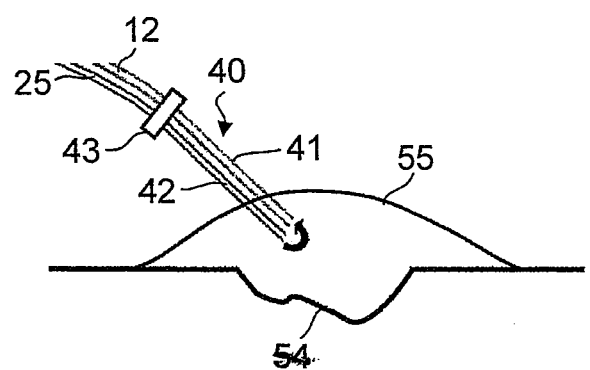
FIG. 6 shows a schematic illustration of wound drainage.

FIGS. 5 and 6 illustrate further application examples of a suction apparatus according to the invention. In FIG. 5, the double-lumen catheter 40 is inserted into the mediastinum. In FIG. 6, the double-lumen catheter 40 opens into an area above a wound 54 which is covered with a fluid-tight covering 55. In particular, in this embodiment, the catheter 40 can also be entirely omitted, and the drainage tube 12 and the auxiliary tube 25 can be guided directly into the area above the wound. A multiplicity of different configurations at the end of the drainage line and of the auxiliary line are conceivable. For example, it is conceivable to conduct the air supplied by the auxiliary line 25, 42 onto the wound over a large area thereof and to suck the air off centrally towards the drainage line 12, 41.

Figure 7:
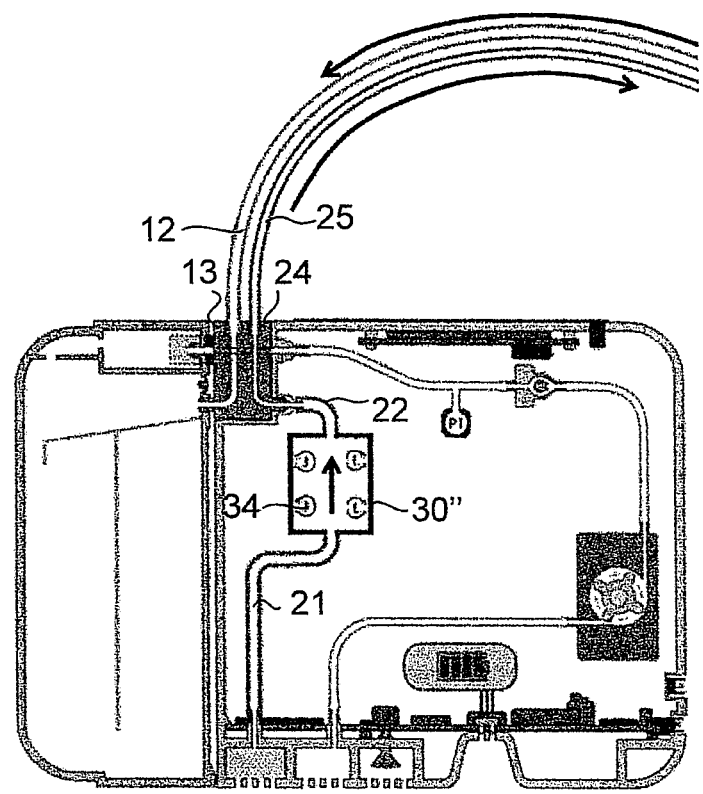
FIG. 7 shows a schematic illustration of a further exemplary embodiment of a suction apparatus with a sterilizing cell.

FIG. 7 illustrates a further embodiment of a suction apparatus with a sterilizing cell. The sterilizing cell in FIG. 7 is designed as a pure continuous flow cell 30" having a constant volume. In the present example, no valves of any sort are provided. However, it is conceivable to provide a valve at least at the inlet or at the outlet of the sterilizing cell in order to control when sterilized air is to be supplied to the auxiliary line 25.

In all of the embodiments, the sterilizing cell can be integrated either fixedly in the pump assembly housing, or it can be retrofittable and/or interchangeable. For this purpose, the sterilizing cell can have connecting elements in order releasably to connect the sterilizing cell to the pump assembly housing 10 and/or to the fluid collection container 11. Examples of connecting structures of this type can include snap-in latches.

Of course, diverse modifications of the exemplary embodiments illustrated are possible without departing from the scope of the present invention, and the invention is in no way restricted to the exemplary embodiments. In particular, the drainage connection can also be formed, for example, directly on the fluid collection container. The suction apparatus does not necessarily have to be a portable, digital apparatus but may also be an apparatus of a conventional type for connection to a hospital vacuum system. Accordingly, instead of a fluid collection container of the type illustrated here, a conventional fluid collection system with a water lock can also be provided (as a one-, two- or three-cylinder system), as has long been known from the prior art.

The invention claimed is:

1. A suction apparatus for aspirating a fluid from a human or animal body by means of negative pressure, the suction apparatus comprising:
a pump assembly housing;
a drainage connection for a drainage line for removing the fluid from the body;
a vacuum source arranged in the pump assembly housing, for generating a negative pressure at the drainage connection in order to suck up the fluid through the drainage line;
a fluid collection container for collecting the sucked-up fluid;
an auxiliary connection for an auxiliary line; and
a sterilizing device with a sterilizing cell arranged in the pump assembly housing, wherein the sterilizing cell has an inlet in order to supply a gas to the sterilizing cell, wherein the sterilizing device is configured to treat the supplied gas in such a manner that pathogens contained in said gas are modified and thereby rendered harmless, and wherein the sterilizing cell has an outlet in order to conduct the treated gas out of the sterilizing cell to the auxiliary connection, and
wherein the sterilizing device comprises an inlet valve at the inlet of the sterilizing cell, through which inlet valve the gas can be supplied to the sterilizing cell, and an outlet valve at the outlet of the sterilizing cell, through which outlet valve the treated gas can be conducted out of the sterilizing cell, such that the inlet valve and the outlet valve act as a lock for the supplied gas entering the sterilizing cell.

2. The suction apparatus according to claim 1, wherein the inlet is connected to an environmental space in order to supply ambient air to the sterilizing cell.

3. The suction apparatus according to claim 1, wherein the sterilizing device comprises a treatment device in order to treat the supplied gas by means of UV rays, by increasing a temperature and/or by an action of steam.

4. The suction apparatus according to claim 3, wherein the treatment device comprises at least one UV light source.

5. The suction apparatus according to claim 3, wherein the treatment device comprises at least one heat source.

6. The suction apparatus according to claim 1, wherein the suction apparatus comprises a control device which is configured to carry out the following steps:
(a) closing the outlet valve;
(b) opening the inlet valve in order to supply the gas to the sterilizing cell;
(c) closing the inlet valve;
(d) treating the supplied gas in the sterilizing cell in such a manner that pathogens contained in said gas are modified and thereby rendered harmless; and
(e) opening the outlet valve in order to conduct the treated gas out of the sterilizing cell, wherein step (b) is carried out before, during or after step (a), wherein step (c) is carried out after step (b), and wherein step (d) is carried out at least between step (c) and step (e).

7. The suction apparatus according to claim 1, wherein the sterilizing cell has a variable volume.

8. The suction apparatus according to claim 7, wherein the sterilizing cell has a cylindrical wall region and a plunger disposed therein, wherein the plunger is displaceable within the cylindrical wall region in order to change the volume of the sterilizing cell.

9. The suction apparatus according to claim 7, wherein the sterilizing cell has an elastic or expansion-bellows-like wall region in order to change the volume of the sterilizing cell.

10. The suction apparatus according to claim 7, wherein the sterilizing device comprises a spring element which is designed and arranged in such a manner that it tends to maximize the variable volume.

11. The suction apparatus according to claim 7, wherein the sterilizing device comprises a drive in order to actively change the volume of the sterilizing cell.

12. The suction apparatus according to claim 1, wherein the sterilizing cell is designed as a continuous flow cell having a constant volume.

13. The suction apparatus according to claim 1, wherein the suction apparatus comprises the drainage line which is connected to the drainage connection,
wherein the suction apparatus comprises the auxiliary line which is connected to the auxiliary connection, and
wherein an apparatus-remote end of the auxiliary line is in fluid-communicating connection with an apparatus-remote end of the drainage line.

14. The suction apparatus according to claim 1, wherein the sterilizing cell is retrofittable and/or interchangeable.

15. A sterilizing device for a suction apparatus for aspirating a fluid from a human or animal body by means of negative pressure, the suction apparatus comprising a pump assembly housing;
a drainage connection for a drainage line for removing fluid from the body;
a vacuum source arranged in the pump assembly housing for generating a negative pressure at the drainage connection in order to suck up the fluid through the drainage line; wherein the sterilizing device comprises a sterilizing cell which is provided with an inlet in order to supply a gas to the sterilizing cell, wherein the sterilizing device is configured to treat the supplied gas in such a manner that pathogens contained in the supplied gas are modified and thereby rendered harmless, in order to reduce a risk of the human or the animal body being infected by the supplied gas, wherein the sterilizing cell has an outlet, and wherein the sterilizing device comprises an inlet valve at the inlet of the sterilizing cell such that the supplied gas is supplied through the inlet valve to the sterilizing cell, and an outlet valve at the outlet of the sterilizing cell such that the treated gas is conducted through the outlet valve out of the sterilizing cell, and wherein the inlet valve and the outlet valve act as a lock for the supplied gas entering the sterilizing cell.

16. The sterilizing device according to claim 15, wherein the inlet is connected to an environmental space in order to supply ambient air to the sterilizing cell.

17. The sterilizing device according to claim 15, wherein the sterilizing device comprises a treatment device in order to treat the supplied gas by means of UV rays, by increasing a temperature and/or by an action of steam.

18. The sterilizing device according to claim 15, wherein the sterilizing cell has a variable volume.

19. The sterilizing device according to claim 15, wherein the sterilizing device comprises a spring element which is designed and arranged in such a manner that it tends to maximize the variable volume of the sterilizing cell.

20. The sterilizing device according to claim 15, wherein the sterilizing device comprises a drive in order to actively change the volume of the sterilizing cell.

21. A method for supplying air to an auxiliary line of a suction apparatus, wherein the suction apparatus comprises:
  a pump assembly housing;
  a drainage line; and
  a vacuum source arranged in the pump assembly housing, for generating a negative pressure, in order to aspirate a fluid from a human or animal body through the drainage line by means of the negative pressure,
  a sterilizing cell being arranged in the pump assembly housing and having an inlet and an outlet;
  an inlet valve at the inlet of the sterilizing cell; and
  an outlet valve at the outlet of the sterilizing cell;
  and wherein an apparatus-remote end of the auxiliary line is in fluid-communicating connection with an apparatus-remote end of the drainage line, the method comprising the following steps:
(a) closing the outlet valve;
(b) opening the inlet valve in order to supply the gas to the sterilizing cell;
(c) closing the inlet valve;
(d) treating the supplied gas in the sterilizing cell in such a manner that pathogens contained in the gas are modified and thereby rendered harmless; and
(e) opening the outlet valve in order to conduct the treated gas out of the sterilizing cell to the auxiliary line,
wherein step (b) is carried out before, during or after step (a), wherein step (c) is carried out after step (b), and wherein step (d) is carried out at least between step (c) and step (e).

22. The method according to claim 21, wherein the supplied gas is ambient air from an environmental space.

23. The method according to claim 21, wherein the supplied gas is treated by means of UV rays, by increasing a temperature and/or by an action of steam.

24. The method according to claim 21, wherein the volume of the sterilizing cell is changeable while the gas is being supplied to the sterilizing cell and/or while the treated gas is being conducted out of the sterilizing cell.

25. A suction apparatus for aspirating a fluid from a human or animal body, the suction apparatus comprising:
  a pump assembly housing;
  a drainage tube;
  a fluid collection container in communication with the drainage tube;
  a vacuum source arranged in the pump assembly housing, in communication with both of the drainage tube and the fluid collection container;
  an auxiliary tube; and
  a sterilizing device having a sterilizing cell arranged in the pump assembly housing, wherein the sterilizing cell has an inlet in communication with an inlet tube, wherein the sterilizing device includes at least one of an ultraviolet source, a heat source, a steam generator, an ozone generator, an electron source or a gamma radiation source, and wherein the sterilizing cell has an outlet in communication with an outlet tube, wherein the outlet tube is in communication with the auxiliary tube, and
  wherein the sterilizing device comprises an inlet valve at the inlet of the sterilizing cell, through which inlet valve the gas can be supplied to the sterilizing cell, and an outlet valve at the outlet of the sterilizing cell, through which outlet valve the treated gas can be conducted out of the sterilizing cell, such that the inlet valve and the outlet valve act as a lock for the supplied gas entering the sterilizing cell.

26. A sterilizing device for a suction apparatus for aspirating a fluid from a human or animal body, the suction apparatus comprising a pump assembly housing;
  a drainage connection for a drainage line for removing fluid from the body;
  a vacuum source arranged in the pump assembly housing for generating a negative pressure at the drainage connection in order to suck up the fluid through the drainage line; wherein the sterilizing comprises:
  a sterilizing cell having an inlet in communication with an atmosphere, wherein the sterilizing device includes at least one of an ultraviolet source, a heat source, a steam generator, an ozone generator, an electron source or a gamma radiation source, in order to reduce a risk of the human or the animal body being infected by a supplied gas, and wherein the sterilizing cell has an outlet configured to permit air to exit the sterilizing cell,
  an inlet valve at the inlet of the sterilizing cell such that the supplied gas is supplied through the inlet valve to the sterilizing cell, and
  an outlet valve at the outlet of the sterilizing cell such that the treated gas is conducted through the outlet valve out of the sterilizing cell,
  wherein the inlet valve and the outlet valve act as a lock for the supplied gas entering the sterilizing cell.

* * * * *